(12) United States Patent
Klassen et al.

(10) Patent No.: US 9,052,798 B1
(45) Date of Patent: Jun. 9, 2015

(54) MEDIA, SYSTEMS, AND METHODS FOR GAME-BASED EXERCISE TRACKING WITH VIRTUAL WORLD VARIATIONS

(71) Applicant: Rally Health, Inc., Washington, DC (US)

(72) Inventors: Ian H. Klassen, Campbell, CA (US); Marc Vincent Raymond, Sausalito, CA (US); Horacio Perez, San Francisco, CA (US); Daniel Lawrence Staley, Washington, DC (US)

(73) Assignee: Rally Health, Inc., Washington, DC (US)

( * ) Notice: Subject to any disclaimer, the term of this patent is extended or adjusted under 35 U.S.C. 154(b) by 0 days.

(21) Appl. No.: 14/446,901

(22) Filed: Jul. 30, 2014

(51) Int. Cl.
| | |
|---|---|
| *A63F 9/24* | (2006.01) |
| *G06F 3/0481* | (2013.01) |
| *G06F 17/30* | (2006.01) |
| *H04L 12/58* | (2006.01) |

(52) U.S. Cl.
CPC ...... *G06F 3/04815* (2013.01); *G06F 17/30241* (2013.01); *H04L 51/04* (2013.01)

(58) Field of Classification Search
CPC . A63B 69/00; G09B 19/0038; G09B 19/3481
USPC .............................................. 463/7; 434/247
See application file for complete search history.

(56) References Cited

U.S. PATENT DOCUMENTS

| | | | |
|---|---|---|---|
| 2006/0022833 A1* | 2/2006 | Ferguson et al. .......... 340/573.1 |
| 2007/0146116 A1 | 6/2007 | Kimbrell | |
| 2010/0267521 A1 | 10/2010 | Matsunaga | |
| 2012/0221495 A1 | 8/2012 | Landers | |
| 2012/0283855 A1 | 11/2012 | Hoffman et al. | |
| 2013/0040714 A1* | 2/2013 | Rosing .............................. 463/7 |
| 2013/0052620 A1* | 2/2013 | Franklin et al. ............... 434/236 |
| 2013/0115584 A1* | 5/2013 | Gordon et al. ................ 434/247 |

OTHER PUBLICATIONS

Moves for iPhone, v1.8 [online], retrieved from the Internet at http://www.moves-app.com/ on Sep. 17, 2013.
MapMyWalk GPS Walking, Android Apps on Google Play, MapMyFitness, Inc., Aug. 28, 2013 [online], retrieved from the Internet at https://play.google.com/store/apps/details?id=com.mapmywalk.android2&hl=en on Sep. 17, 2013.
RunKeeper—GPS Track Run Walk, FitnessKeeper, Inc., Sep. 4, 2013 [online], retrieved from the Internet at https://play.google.com/store/apps/details?id=com.fitnesskeeper.runkeeper.pro on Sep. 17, 2013.
My Tracks, Google Inc., Health and Fitness, Aug. 9, 2013 [online], retrieved from the Internet at https://play.google.com/store/apps/details?id=com.google.android.maps.mytracks&hl=en on Sep. 17, 2013.
Runtastic apps—Runtastic—makes sports funtastic [online], retrieved from the Internet at http://www.runtastic.com/en/apps/runtastic on Sep. 17, 2013.
Mapmyride, Moble Cycling App, Bicycle GPS Tracking, Cycling Training Apps [online], retrieved from the Internet at http://www.mapmyride.com/app/ on Sep. 17, 2013.

* cited by examiner

*Primary Examiner* — Corbett B Coburn
(74) *Attorney, Agent, or Firm* — Cooley LLP (57) ABSTRACT

A compute device can receive a signal associated with a quantity of real-world activity (e.g., exercise) performed by a user. The compute device can define a quantity of virtual activity based, at least in part, on the quantity of real-world activity. The quantity of virtual activity can be different from the quantity of real-world activity. The compute device can send an indication of progress in a virtual world to an output device, for example, such that the user's progress is displayed.

20 Claims, 4 Drawing Sheets

MEDIA, SYSTEMS, AND METHODS FOR GAME-BASED EXERCISE TRACKING WITH VIRTUAL WORLD VARIATIONS

BACKGROUND

Some embodiments described herein relate to tracking and gamification of physical exercise.

Some known methods for exercise tracking include detecting a user's location during exercise via global positioning system (GPS) sensors and mapping the user's progress. While such known methods may be suitable for tracking an individual user, they may not adequately motivate the user or allow multiple users of different fitness levels, starting points, and geographic locations to realistically compete against and motivate each other. A need therefore exists for media, systems, and methods for game-based exercise tracking with virtual world variations that can challenge a user to complete a circuit on a virtual world or allow users of different skill levels and starting points to realistically compete against each other.

SUMMARY

A compute device can receive a signal associated with a quantity of real-world activity (e.g., exercise) performed by a user. The compute device can define a quantity of virtual activity based, at least in part, on the quantity of real-world activity. The quantity of virtual activity can be different from the quantity of real-world activity. The compute device can send an indication of progress in a virtual world to an output device, for example, such that the user's progress is displayed.

DETAILED DESCRIPTION

A user can engage in a quantity of real-world activity which can be tracked by a device associated with the user, such as a GPS-enabled mobile phone. The real-world activity can be converted into virtual activity, which can be presented as progress through a virtual world. A scaling factor can be used to convert the real-world activity into the virtual activity. The scaling factor can be based, at least in part, on virtual terrain of the virtual world, the fitness of the user, activity history of the user, and/or any other suitable factor. In some embodiments, the user can compete against other users within the virtual world. Other users can similarly interact with the virtual world by engaging in real-world activity.

Some embodiments described herein relate to tracking user activity in the real-world, which may include tracking walking, running, biking, etc. outdoors or on exercise equipment, such as a treadmill or stationary bike. Real-world activity can be captured by a monitoring device such as, for example, a GPS-enabled mobile phone or communication device.

Some embodiments described herein relate to a virtual world. A virtual world can be, for example, a computer model of a landscape and can include one or more paths. The virtual world, including the path, can have a virtual terrain such as plains, hills, mountains, etc. Some embodiments herein refer to a location of a user in the virtual world. The location of the user can be a virtual location, for example, along the path. In some instances, the user can traverse the path from a beginning of the path to an end point, waypoint, or goal.

Some embodiments described herein relate to virtual activity. As described in further detail herein, virtual activity can be based, at least in part on real-world activity of the user. If a user engages in the real-world activity of walking a mile across flat terrain, that real-world activity can be scaled to the virtual world. For example, if the user is on flat virtual terrain, the real-world activity can be scaled one-to-one, such that the user travels one virtual mile. As another example, if the user is on hilly virtual terrain, the real world activity can be scaled down, such that the user travels less than one virtual mile for every real-world mile.

In some embodiments, a method can include receiving a signal associated with a quantity of real-world activity performed by a user. For example, a device associated with the user, such as a GPS-enabled mobile phone can track the real-world activity of the user and send a signal associated with the real-world activity to, for example, a virtual mapping device. The real-world activity can be converted to a quantity of virtual activity by applying a scaling factor to the quantity of real-world activity. The scaling factor can be based, at least in part, on virtual terrain of the virtual world, the fitness of the user, activity history of the user, and/or any other suitable factor. A signal can be sent, for example, to the user's mobile phone including an indication of progress in the virtual world.

In some embodiments, a method can include receiving a signal associated with a quantity of real-world activity performed by a first user from a first user device, such as a mobile phone. A first quantity of virtual activity can be defined by applying a first scaling factor to the quantity of real-world activity performed by the first user. The first scaling factor can be based, at least in part, on a profile of the first user and/or the location of the first user in the virtual world. A signal associated with a quantity of real-world activity performed by a second user can be received from a second user device. A second quantity of virtual activity can defined by applying a second scaling factor to the quantity of real-world activity performed by the second user. The second scaling factor can be based, at least in part, on a profile of the second user and/or the location of the second user in the virtual world. A comparison of the first quantity of virtual activity and the second quantity of virtual activity can be sent, for example, to the first user device and/or the second user device.

In some embodiments, an indication of a position of a first user and a second user in a virtual world can be received. For example, a server and/or compute device, such as a virtual mapping device can send a signal to, for example, a mobile phone indicating where the first user is located in the virtual world such that an output device (e.g., the display of the mobile phone) presents a representation of the virtual world including the position of the first user and the position of the second user. A signal associated with real-world activity of the second user can be received. In response, a signal can be sent such that the output device can update the position of the second user. For example, display can indicate the second user has a first position before receiving the signal associated with the real-world activity of the second user and a second position (e.g., further along a path) after receiving the signal associated with the real-world activity of the second user.

Figure 1:
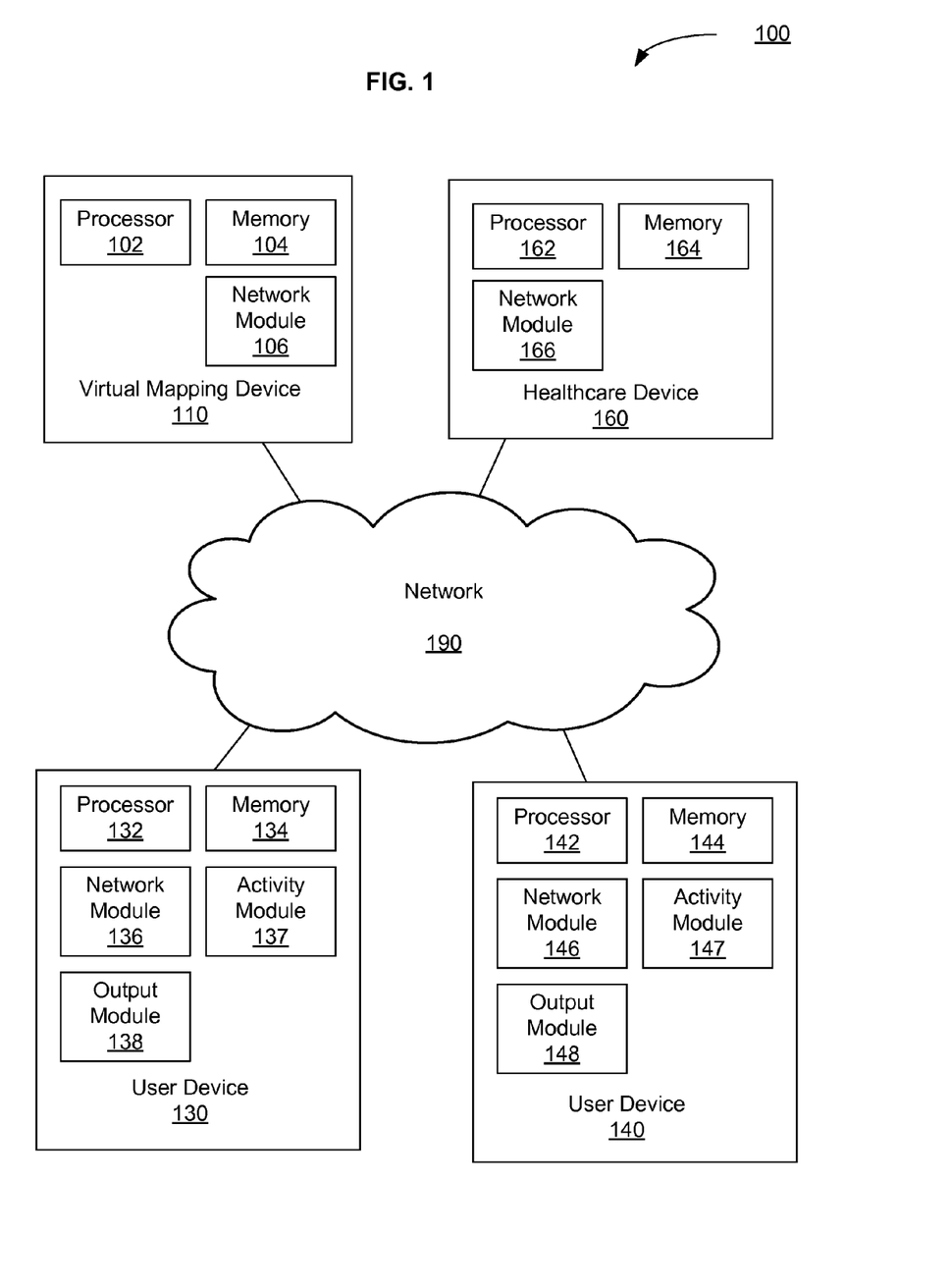
FIG. 1 is a schematic diagram of game-based exercise tracking system, according to an embodiment.

FIG. 1 is a schematic diagram of a game-based exercise tracking system 100 (also referred to herein as "tracking system 100"), according to an embodiment. The system 100 includes a virtual mapping device 110, two user devices 130 and 140, and a healthcare device 160, each communicatively coupled via a network 190.

The first user device 130 can be a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), a GPS device, such as a GPS watch, and/or any other suitable computing entity. The first user device 130 includes a processor 132, a memory 134, a network module 136, an activity module 137, and an output module 138.

The processor 132 can be, for example, a general purpose processor, a Field Programmable Gate Array (FPGA), an Application Specific Integrated Circuit (ASIC), a Digital Signal Processor (DSP), and/or the like. The processor 132 can be configured to retrieve data from and/or write data to memory, e.g., the memory 134, which can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth.

The network module 136 can be a wireless transmission module operable to communicatively couple the user device 130 to the network 190. For example, the network module 136 can be a wired or wireless network interface controller (NIC), a cellular telephone module, a Bluetooth® module, a ZigBee® module, ultrasonic, magnetic and/or any other suitable module configured to send and/or receive signals via the network 190.

The activity module 137 can be a GPS module, an accelerometer, and/or any other suitable module to detect real-world activity of the user when the user carries and/or wears the user device 130. For example, a GPS module can track the location of the user device 130 as it is carried by the user. In this way, the activity module 137 can track a distance traveled and/or speed of the user, when the user walks, runs, bikes, etc. in the real world. As another example, the activity module 137 can be an accelerometer that can function similar to a pedometer monitoring user real-world activity by counting the user's steps. For example, an accelerometer can detect an acceleration profile, which can include magnitude, direction, timing, etc. of movement of the accelerometer/mobile communication device. The activity module 137 can be operable to calculate and/or infer the type, intensity, and/or duration of a real-world activity based on the acceleration profile. For instance, based on the frequency of acceleration spikes, the activity module 137 can be operable to determine whether the user is walking or running. Furthermore, based on information and/or assumptions of stride length, an accelerometer-based activity module 137 can calculate speed and/or distance traveled.

The output module 137 can be any suitable module operable to output a human-perceivable signal, such as a visual display (e.g., a light emitting diode (LED) display, a cathode ray tube (CRT), etc.), a speaker, a haptic output device, etc. In some embodiments, the output module 137 can be operable to display the virtual world and/or indications of real-world activity and/or virtual activity.

The second user device 140, can be structurally and/or functionally similar to the first user device 130. For example, each of a processor 142, a memory 144, a network module 146, an activity module 147, and/or an output module 148 can be structurally and/or functionally similar to the processor 132, the memory 134, the network module 136, the activity module 137, and/or the output module 138, respectively. The second user device 140 can be carried and/or worn by a second user. In this way, the first user device 130 can track the real-world activity of the first user, and the second user device 140 can track the real-world activity of the second user.

The virtual mapping device 110 can be a compute device, such as a server. The virtual mapping device 110 includes a processor 102, a memory 104, and a network module 106, each of which can be structurally similar to the processor 132, the memory 134, and/or the network module 136, respectively. As described in further detail herein, the virtual mapping device 110 can be operable to define a virtual world, track the virtual activity of the first user and/or the second user, set goals, etc.

The healthcare device 160 can be a compute device, such as a server. The healthcare device 160 includes a processor 162, a memory 164, and a network module 166, each of which can be structurally similar to the processor 132, the memory 134, and/or the network module 136, respectively. In some embodiments, the healthcare device 160 is associated with a health insurance provider and/or a healthcare provider. As described in further detail herein, the healthcare device 160 can be operable to send signals associated with user health, fitness, and/or activity goals to the virtual mapping device 110 and/or the user devices 120, 130.

The user devices 120, 130, the virtual mapping device 110, and/or the healthcare device 160 can be communicatively coupled via the network 190. The network 190 can be the Internet, an intranet, a local area network (LAN), a wide area network (WAN), a virtual network, a telecommunications network, any other suitable communication system and/or combination of such networks. The network 190 can be implemented as a wired and/or wireless network.

Figure 2:
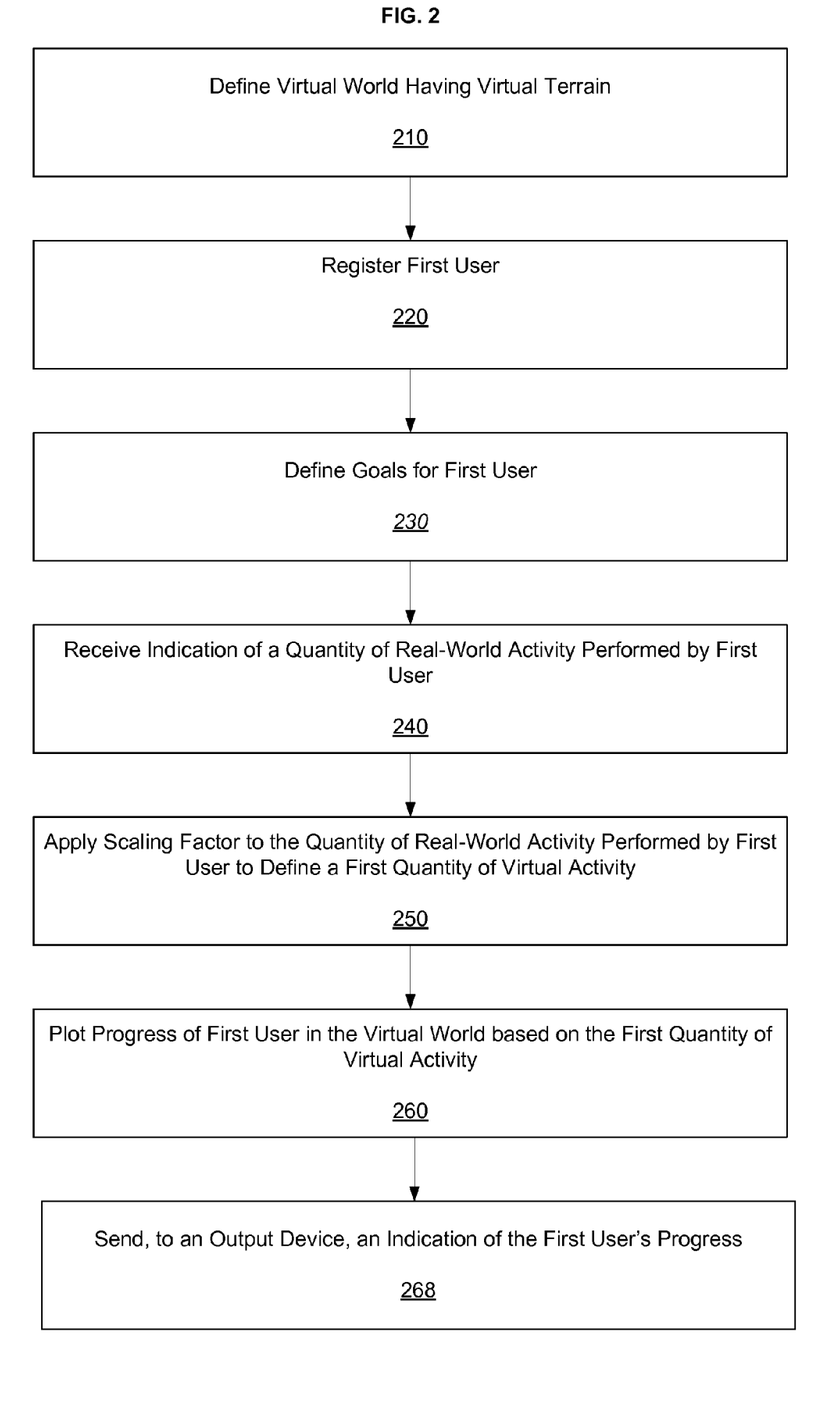
FIGS. 2 and 3 are flowcharts of methods for tracking a user's exercise in a virtual world, according to two embodiments.

FIG. 2 is a flowchart of a method of converting real world activity of a first user to virtual activity, according to an embodiment. In some embodiments, the method illustrated in FIG. 2 is executed on a processor, for example, the processor 102 of the virtual mapping device 110, and/or the processor 132 of the first user device 130.

At 210, a virtual world can be defined. Defining the virtual world, at 210, can include generating and/or rendering a model of a landscape. The model can be, for example, a two or three dimensional model of the landscape, and can be displayed in a static manner or alternatively in a dynamic manner. The virtual world can include virtual terrain, such as plains, hills, mountains, etc., a virtual path, and/or any other suitable virtual feature. In some embodiments, the virtual world corresponds with a real-world location. In other embodiments, the virtual world does not correspond with any real-world location.

As described in further detail herein, a scaling factor, which can represent, at least in part, the difficulty of crossing the virtual terrain can be associated with the virtual terrain. For example, virtual mountains can have a relatively low scaling factor, while virtual plains can have a relatively high scaling factor. For example, a single unit of real-world activity can translate into a greater quantity of virtual activity on a virtual plain than on a virtual mountain.

The virtual path can represent a route through the virtual landscape. For example, when a user interacts with the virtual world (as described in further detail herein) the user's position on the virtual path can change. Similarly stated, a user can have a first position on the virtual path at a first time, then the user can interact with the virtual world (e.g., by engaging in real-world activity) resulting in the user having a second position further along the virtual path at a second time.

A first user can be registered, at 220. Registering the first user, at 220, can include receiving a signal indicating that the first user (who, for example, can be associated with the first user device 130 as shown and described above with reference to FIG. 1) is interested in interacting with the virtual world. For example, registering the first user at 220 can include receiving a signal including the user's real name, username, fitness level, etc. In addition or alternatively, registering the first user at 220 can include receiving an indication of a device (e.g., the user device 130) associated with the first user and operable to provide real-world activity data. Information associated with the registration of the first user can be stored (e.g., in memory) such that the information can be retrieved and/or associated with future interactions with the first user (e.g., signals sent to and/or from the mobile communication device of the first user).

Fitness goals can be defined for the first user, at 230. The fitness goals defined at 230 can be based, for example, on the first user's age, weight, fitness level, past physical activities, input from the first user, etc. A real-world fitness goal, such as, for example, run ten miles, can be converted into a virtual fitness goal, at 230. For example, a goal post can be defined in the virtual world such that the user will reach the goal post after running ten real-world miles. In some embodiments the goal post can be ten virtual miles from the user's position in the virtual world (e.g., at a starting point). In other embodiments, the goal posts can be more or less than ten virtual miles from the user's position. For example, the distance between the goal posts and the user can be selected based on, for example, the virtual terrain and/or a representation of distance likely to motivate the user.

In some embodiments, defining the fitness goals, at 230 can include receiving a signal from a healthcare provider and/or an insurance provider associated with medical data associated with the first user. For example, the healthcare device 160, as shown and described above with reference to FIG. 1, can send medical and/or demographic data associated with the first user to the virtual mapping device 110. In some such embodiments, a signal received from the healthcare device 160 can include private healthcare information. Private healthcare information can be used to set goals, at 230, that are individually tailored to the first user based on doctor advice and/or diagnostic medical data. In such an embodiment, the operator of the virtual mapping device 110 can have a preexisting agreement with the operator of the healthcare device 160, which can include data access and/or data security agreements. Similarly stated, setting fitness goals, at 230 can include setting goals based on non-public and/or non-user provided information such as, for example, data collected by medical professionals such as weight, body mass index, fitness, cardiac health information, pulmonary function information. Such information can include, for example, data protected by Health Insurance Portability and Accountability Act (HIPAA) regulations, and can be maintained, accessed and modified according to the HIPAA regulations.

At 240, a signal can be received, for example, from the first user device 130, that includes an indication of a quantity of real-world activity performed by the first user. For example, the first user can engage in a real-world activity, such as running, walking, biking, etc., monitored by the first user device 130. The first user device 130 can send the signal associated with the real-world activity during the real-world activity and/or after the activity is completed. The signal received, at 240, can include information such as the duration of the real-world activity, a distance the first user covered while undertaking the real-world activity, the intensity of the real-world activity (e.g., pace information, information regarding changes in altitude, etc.), the type of real-world activity, and/or any other suitable information.

A scaling factor can be applied to the quantity of real world activity, at 250. The application of the scaling factor, at 250 can be operable to convert the quantity of real world activity to a quantity of virtual world activity. For example, an indication of a quantity real-world activity, at 240, such as, for example, "walked three (real-world) miles," can be converted into a quantity of virtual world activity by applying a scaling factor, at 250. For example, the three miles of real-world activity can be converted to, for example, two virtual world miles.

The scaling factor can be selected based, at least in part, on the virtual world terrain, the fitness goals of the user, past (real-world and/or virtual) activities performed by the first user, the goals defined at 230, the type, intensity, and/or any other information associated with the real-world activity, and/or any other suitable factor. For example, a location of the user within the virtual world can be determined, and a virtual terrain can be associated with the first user's virtual position. If the first user has a virtual position on a plain within the virtual world, a relatively high base scaling factor can be selected, such as 100%, 125%, or any other suitable scaling factor. The base scaling factor can be adjusted based on, for example, the users goals, fitness level, etc. For example, if the first user is relatively fit and healthy, the base scaling factor can be adjusted down. Similarly, if the first user has a relatively aggressive fitness goal, (e.g., run 100 miles in a month), the base scaling factor can again be adjusted down, such that the first user gets less virtual "credit" for his real-world activity to normalize or handicap him or her against other users who may be traveling the same virtual path and who may be less fit or may have relatively less aggressive fitness goals. Conversely, if the first user is relatively out of shape and/or unhealthy, the base scaling factor can be adjusted up, such that the relatively out of shape first user can receive relatively more virtual credit, which may provide motivation for the first user to continue exercising by enabling him or her to compete in the virtual world against other users who may be more fit and may engage in more rigorous real-world activities.

The first user's progress in the virtual world can be plotted, defined, and/or calculated, at 260. For example, based on the quantity of virtual-world activity defined, at 250, the user's position along a path in the virtual world can be determined. In some embodiments, plotting the progress of the first user, at 260, can include sending a signal, at 268, operable to cause an output device to render a representation of the first user's progress in the virtual world. For example, the virtual mapping device 110 can send a signal to the first user device 130 associated with the quantity of virtual activity defined at 250. In some embodiments, plotting the first user's progress, at 260, can include displaying motivational messages, such as messages intended to congratulate the user, messages intended to encourage the user to continue engaging in real-world activity, and/or messages informing the first user of the position and/or progress of other users (described in further detail herein) intended to cause or motivate the first user to compete against the other users.

The first user device 130, in response to receiving a signal associated with the virtual activity, (e.g., the signal sent at 268) can present a visual display of the virtual world and/or the first user's progress therethrough. In addition or alternatively, the signal sent at 268 can be operable to indicate that the first user has achieved a goal, traveled a particular distance in the virtual world, send a reward (e.g., an electronic gift card), and/or any other suitable indication or reward of progress.

In some instances, the position and/or progress of the first user within the virtual world can be saved (e.g., in the memory 104 and/or 134), for example when the first user device 130 and/or the virtual mapping device 110 is switched off and/or not executing an application (on the processor 132) associated with the method of FIG. 2. In such an instance, signals associated with a quantity of real-world activity can be repeatedly be received (e.g., similar to the signal received at 240). In such an instance, the location of the first user within the virtual world can be repeatedly determined and the terrain associated with the first user's position can be used to select a scaling factor for each quantity of real-world activity. In this way, the user can progress through the virtual world through an accumulation of a series of real-world activities.

Figure 3:
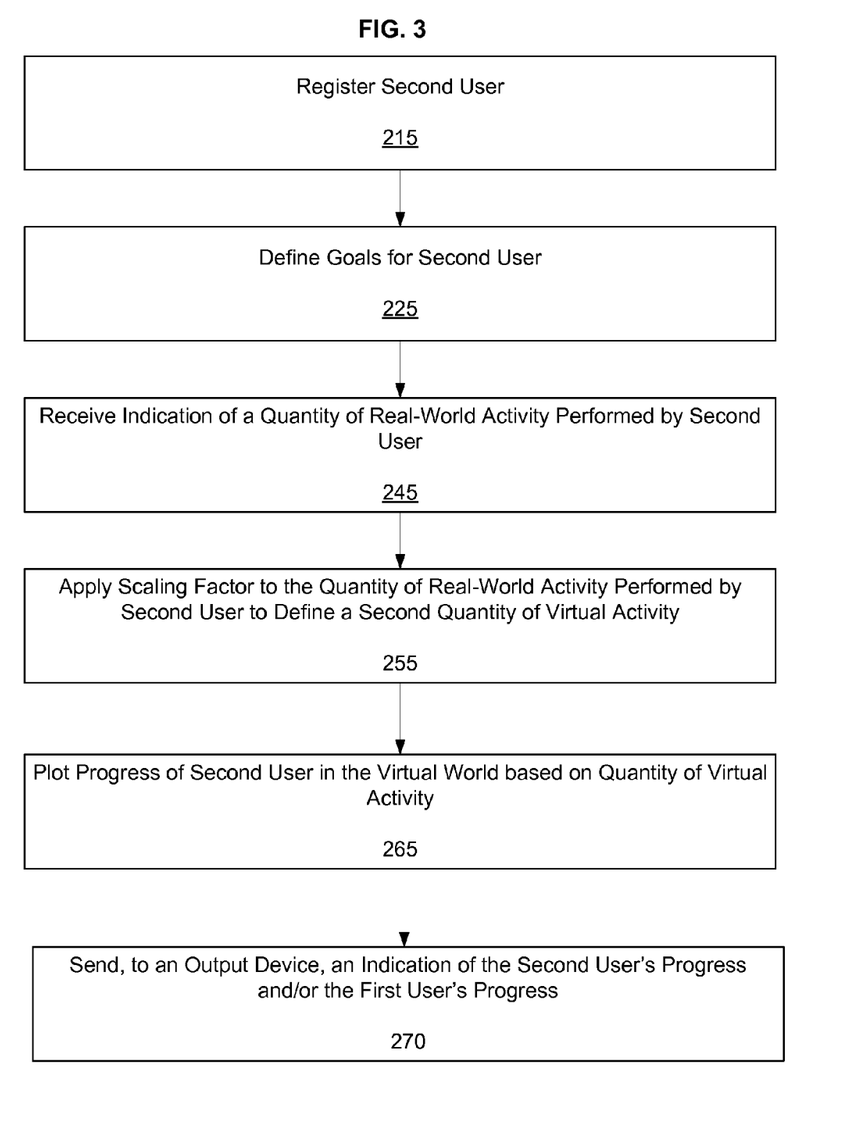

FIG. 3 is a flowchart of a method of converting real-world activity of a second user to virtual activity, according to an embodiment. In some embodiments, the method shown and described above with reference to FIG. 2 can be performed in parallel with the method of FIG. 3. For example, in some embodiments, the methods illustrated in FIGS. 2 and 3 are both executed on the processor 102 of the virtual mapping device 110. In this way, real-world activity of a first user and real-world activity of the second user can both be converted to virtual activity in a common virtual world. Alternatively, the method of FIG. 2 can be executed on one user device (such as user device 130) and the method of FIG. 3 can be executed on another user device (such as user device 140) such that the two user devices share progress information in a peer-to-peer manner or via an intermediary compute device (such as the virtual mapping device 110).

A second user can be registered, at 215, and goals can be defined for the second user, at 225, which can be similar to registering the first user, at 210, and/or defining goals for the first user, at 220, respectively. At 225, an indication of a quantity of real-world activity performed by the second user can be received. For example, the second user device 140, which can be associated with the second user, can track a real-world activity engaged in by the second user. The second user device 140 can be operable to send a signal associated with the quantity of real-world activity (e.g., to the virtual mapping device 110, the first user device 130, and/or the processor 142 of the second user device) which can be received, at 245.

At 255, a scaling factor can be applied to the quantity of real-world activity performed by the second user. Applying the scaling factor, at 255, can be similar to applying the scaling factor at 250. Applying the scaling factor, at 255, can be based, at least in part, on a virtual location of the second user. In some embodiments, the first user and the second user can have different positions on a common path through the virtual world. In some embodiments, the virtual terrain can tend to increase in difficulty along the path. For example, the path can start in plains, then move to hills and/or mountains. In this way, the scaling factor can change the further the first user or the second user travels along the path. Similarly stated, the virtual distance defined per unit of real-world activity can decrease as the first user or the second user travels along the path. As a result, if, for example, the first user is ahead of the second user on the virtual path, the second user can be on easier terrain, which can make it easier for the second user to catch up to the first user. Increasingly difficult terrain can allow a user that is behind to more easily catch up to users that are ahead, which can motivate the trailing user, who may be less likely to feel discouraged and unable to catch the leading users.

At 265, the progress of the second user in the virtual world can be plotted, defined, and/or calculated based on the quantity of virtual activity defined, at 255. Plotting, defining, and/or calculating the progress of the second user at 265 can be similar to plotting the progress of the first user, at 260. At 270, a signal can be sent to an output device including an indication of the second user's progress and/or the first user's progress in the virtual world. For example, the mapping device 110 can send a signal to the first user device 130 and/or the second user device 140 including an indication of the position and/or progress (e.g., an indication of a change in position and/or indications of a series of positions) of the first user and/or of the second user in the virtual world. In this way, the first user can receive an indication of the progress of the second user, such that the first user can determine whether the second user is catching up to the first user's position, passing the first user, etc. The second user can similarly be informed of the progress of the first user. By informing the first user of the second user's progress the first user may be motivated to compete against the second user, which may result in the first user engaging in more real-world physical activity than if the first user were exercising alone.

Figure 4:
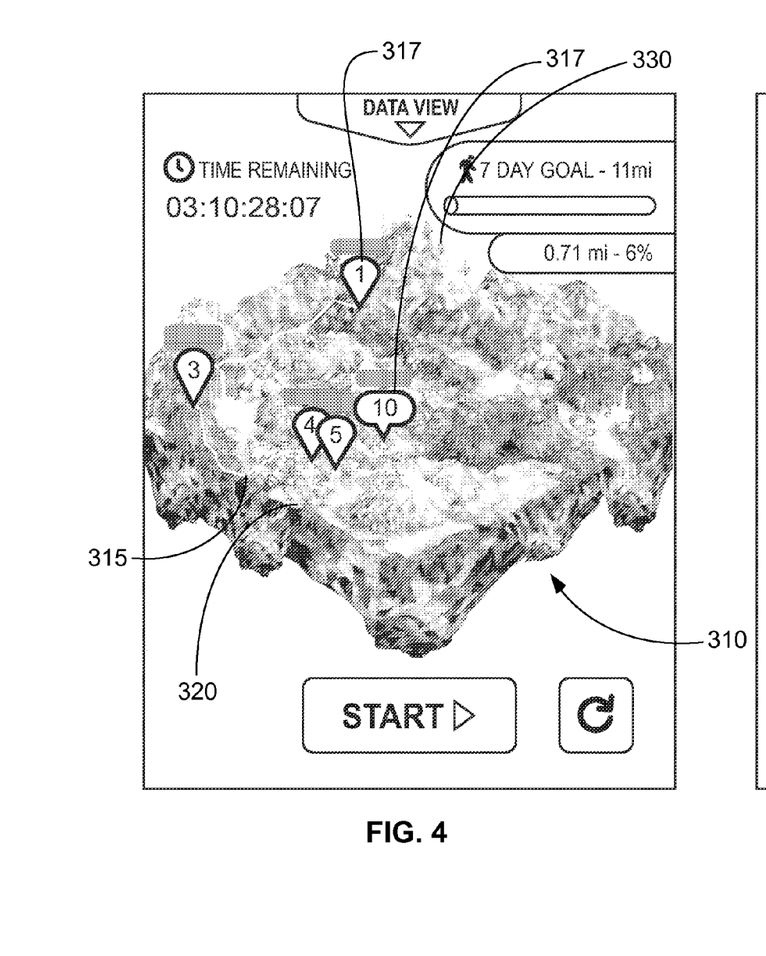
FIGS. 4 and 5 are each a screenshot of a user interface for interacting with a virtual world, according to an embodiment.

FIG. 4 is a screenshot of a user interface depicting a virtual world 310, according to an embodiment. The virtual world 310 includes a path 315. As shown, ten users are interacting with the virtual world 310. Place markers 317 for the first place, third place, fourth place, fifth place, and tenth place users are shown (place markers for the second place, and sixth through ninth places are obscured behind place markers for other users). The place markers 317 can be operable to inform a user of his or her position in the virtual world 310 relative to the other users. The virtual world 310 further includes virtual terrain, such as a relatively flat forest 320 and a relatively steep mountain 330. As shown, the users in fourth through tenth places are on the path 315 in the relatively flat forest 320, while the user in first place is climbing the relatively steep mountain 330. Scaling factors based, at least in part, on the virtual terrain can be used to convert real-world activity into virtual world activity, such that the user in first place has a more difficult time advancing along the virtual path than the users traversing the forest 330. In this way, the scaling factor is based, at least in part, on a history of physical real-world activity of a given user because that user's current position is based on cumulated past physical real-world activity.

Figure 5:
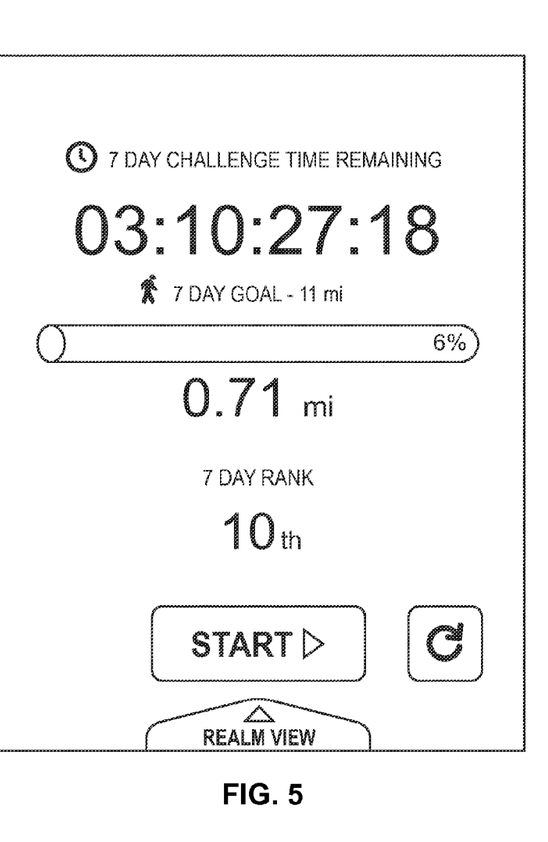

FIG. 5 is a screenshot of a data view of a user interface for a user interacting with the virtual world 310. As shown in FIG. 5, the user for this user interface is engaged in a seven day, virtual eleven-mile competition with the nine other users. The user for this user interface is in tenth place and has traveled 0.71 virtual miles.

While various embodiments have been described above, it should be understood that they have been presented by way of example only, and not limitation. Furthermore, although various embodiments have been described as having particular features and/or combinations of components, other embodiments are possible having a combination of any features and/or components from any of embodiments where appropriate as well as additional features and/or components. For example, while some embodiments are described as having a virtual mapping device, in other embodiments, a user device can include some and/or all of the components of a virtual mapping device and/or can perform some and/or all of the functions of a virtual mapping device.

As another example, although scaling factors are described in some embodiments as being based and/or varying, at least in part, on factors such as virtual terrain, in other embodiments, a quantity of real-world activity can be converted one-to-one and/or at any constant ratio to a quantity of virtual activity.

Although some embodiments described herein refer to tracking real-world activity of a user via GPS, in other embodiments, real-world activity can include activity performed on stationary exercise equipment, such as a treadmill, stationary bike, rowing machine, etc. In such an embodiment, the exercise equipment can send a signal associated with the exercise, and/or the user can input a summary of the activity (e.g., via the user device and/or a web portal).

As yet another example, although some embodiments are described with reference to a first user and a second user, the systems and methods described herein can have a single user and/or be extended to any number of users.

Although some embodiments described herein refer to a user interacting with a virtual world by engaging in real-world activity, such as exercise, in other embodiments the user can interact with the virtual world (e.g., change position on a virtual path) by any other suitable means. For example, in some embodiments, a user can interact with the virtual world by providing information about his or her diet, solving puzzles, completing surveys, providing payment, referring other users, etc.

Although some embodiments describe a user on a virtual path in a virtual world having a virtual terrain, other embodiments can include alternative virtual representations to track, represent, and/or gamify real-world exercise. As one example, although some embodiments describe a difficulty of a virtual terrain associated with a scaling factor, in other embodiments other virtual features can be associated with a scaling factor. For example, rather than traversing a path having increasingly difficult terrain, the user can collect virtual rewards having weight as the user progresses in the virtual world. As the user accumulates more weight, the scaling factor can decrease. As another example, the user can be represented as completing "circuits" of a course, such as a race track, as the user progresses, completing more circuits, the length of the track can increase such that additional real-world activity is required to complete each subsequent circuit. As yet another example, any suitable virtual representation of real-world activity can be used. For instance, rather than traversing a path in a virtual world, a bar or line graph can be completed, a virtual representation of a vessel can be filled, a virtual representation of meter or scale can be adjusted, a virtual score, or virtual currency can be accumulated, etc. In some instances, scaling factors can impact the rate at which virtual progress is made. For example, analogous to the scaling factor associated with virtual terrain described herein, a variable scaling factor can be used to convert real-world activity into progress indicators on the bar or line graph, the rate at which a virtual representation of a vessel is filled, the rate at which a meter or scale is adjusted, and/or the rate at which a virtual score or currency is accumulated.

Where methods described above indicate certain events occurring in certain order, the ordering of certain events may be modified. Additionally, certain of the events may be performed repeatedly, concurrently in a parallel process when possible, as well as performed sequentially as described above.

Some embodiments described herein relate to computer-readable medium. A computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, PLDs, ROM and RAM devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

What is claimed is:

1. A non-transitory processor-readable medium storing code representing instructions to be executed by a processor, the code comprising code to cause the processor to:
   receive, from a first user exercise tracking device, a signal associated with a quantity of real-world activity performed by a first user;
   define a first quantity of virtual activity by applying a first scaling factor to the quantity of real-world activity performed by the first user, the first scaling factor based, at least in part, on at least one of a fitness of the first user, a record of virtual activity of the first user, or an activity type of the real-world activity performed by the first user;
   receive, from a second user exercise tracking device, a signal associated with a quantity of real world activity performed by a second user;
   define a second quantity of virtual activity by applying a second scaling factor to the quantity of real-world activity performed by second user, the second scaling factor different from the first scaling factor; and
   send, to the first user exercise tracking device, a signal associated with a comparison of the first quantity of virtual activity and the second quantity of virtual activity.

2. The non-transitory processor-readable medium of claim 1, wherein the first scaling factor is based, at least in part, on a virtual terrain.

3. The non-transitory processor-readable medium of claim 1, wherein the first scaling factor is based, at least in part, on a virtual terrain, the virtual terrain based, at least in part, on the record of virtual activity of the first user.

4. The non-transitory processor-readable medium of claim 1, wherein:
   the quantity of real-world activity performed by the first user is a first quantity of real-world activity performed by the first user,
   the signal associated with the first quantity of real-world activity performed by the first user is received at a first time,
   the code further comprising code to cause the processor to:
   define a first virtual location of the first user in a virtual world based, at least in part, on the first quantity of real-world activity performed by the first user, the first virtual location having a first virtual terrain, the first scaling factor based, at least in part, on the first virtual terrain;

receive, from the first user exercise tracking device at a second time after the first time, a signal associated with a second quantity of real-world activity performed by the first user;

define a second virtual location of the first user in the virtual world based, at least in part, on the first virtual location and the second quantity or real-world activity performed by the first user, the second virtual location having a second virtual terrain, the second virtual terrain more difficult than the first virtual terrain.

5. The non-transitory processor readable medium of claim 1, the code further comprising code to cause the processor to receive, from at least one of a healthcare provider or a health insurance provider, a signal associated with the fitness of the first user and a fitness of the second user, the first scaling factor based, at least in part, on the fitness of the first user, the second scaling factor based, at least in part, on the fitness of the second user.

6. The non-transitory processor readable medium of claim 1, wherein the signal associated with the first quantity of real-world activity is based on at least one of GPS data associated with the first user exercise tracking device, acceleration data associated with the first user exercise tracking device, or an output of an exercise device.

7. The non-transitory processor readable medium of claim 1, the code further comprising code to cause the processor to:
define a virtual world having a virtual terrain and a virtual path, the first user having a position on the virtual path, the first scaling factor based, at least in part, on the virtual terrain at the position of the first user.

8. A method, comprising:
receiving an indication of a quantity of real-world activity performed by a first user;
defining, at a scaling module, a first quantity of virtual activity by applying a first scaling factor to the quantity of real-world activity performed by the first user, the first scaling factor based, at least in part, on at least one of a fitness of the first user, a record of virtual activity of the first user, or an activity type of the real-world activity performed by the first user, the scaling module implemented in at least one of a processor or a memory;
receiving an indication of a quantity of real-world physical activity performed by a second user;
defining, at the scaling module, a second quantity of virtual activity by applying a second scaling factor to the quantity of real-world activity performed by the second user, the second scaling factor different from the first scaling factor; and
sending an indication associated with a comparison of the first quantity of virtual activity and the second quantity of virtual activity.

9. The method of claim 8, wherein the first scaling factor is based, at least in part, on a virtual terrain, the virtual terrain based, at least in part, on the record of virtual activity for the first user.

10. The method of claim 8, wherein:
the quantity of real-world activity performed by the first user is a first quantity of real-world activity performed by the first user,
the indication of the first quantity or real-world activity performed by the first user is received at a first time,
the method further comprising:
defining a first virtual location of the first user in a virtual world based, at least in part, on the first quantity of real-world activity performed by the first user, the first virtual location having a first virtual terrain, the first scaling factor based, at least in part, on the first virtual terrain;
receiving an indication of a second quantity of real-world activity performed by the first user;
defining a second virtual location of the first user in the virtual world based, at least in part, on the first virtual location and the second quantity or real-world activity performed by the first user, the second virtual location having a second virtual terrain, the second virtual terrain more difficult than the first virtual terrain.

11. The method of claim 8, further comprising:
receiving, from at least one of a healthcare provider or a health insurance provider, an indication of the fitness of the first user and a fitness of the second user, the first scaling factor based, at least in part, on the fitness of the first user, the second scaling factor based, at least in part, on the fitness of the second user.

12. The method of claim 8, wherein the indication of the first quantity of real-world activity is based on at least one of GPS data, acceleration data, or an output of an exercise device.

13. The method of claim 8, further comprising:
defining a virtual world having a virtual terrain and a virtual path, the first user having a position on the virtual path, the first scaling factor based, at least in part, on the virtual terrain at the position of the first user.

14. An apparatus, comprising:
a network module configured to receive a signal associated with a quantity of real-world activity performed by a first user and a signal associated with a quantity or real world activity performed by a second user;
a scaling module operatively coupled to the network module, the scaling module being implemented in at least one of a processor or a memory, the scaling module configured to:
define a first quantity of virtual activity by applying a first scaling factor to the quantity of real-world activity performed by the first user, the first scaling factor based, at least in part, on at least one of a fitness of the first user, a record of virtual activity of the first user, or an activity type of the real-world activity performed by the first user; and
define a second quantity of virtual activity by applying a second scaling factor to the quantity of real-world activity performed by second user, the second scaling factor different from the first scaling factor.

15. The apparatus of claim 14, wherein:
the signal associated with the first quantity of real-world activity is received from a first user exercise tracking device;
the signal associated with the second quantity of real-world activity is received from a second user exercise tracking device; and
the network module is configured to send a signal associated with a comparison of the first quantity of virtual activity and the second quantity of virtual activity to at least one of the first user exercise tracking device or the second user exercise tracking device.

16. The apparatus of claim 14, wherein the first scaling factor is based, at least in part, on a virtual terrain.

17. The apparatus of claim 14, wherein the first scaling factor is based, at least in part, on a virtual terrain, the virtual terrain based, at least in part, on the record of virtual activity of the first user.

18. The apparatus of claim 14, wherein:
- the quantity of real-world activity performed by the first user is a first quantity of real-world activity performed by the first user,
- the signal associated with the first quantity of real-world activity performed by the first user is received at a first time,
- the network module is further configured to receive a signal associated with a second quantity of real-world activity performed by the first user,
- the apparatus further comprising a virtual world module operatively coupled to the scaling module, the virtual world module configured to:
  - define a first virtual location of the first user in a virtual world based, at least in part, on the first quantity of real-world activity performed by the first user, the first virtual location having a first virtual terrain, the first scaling factor based, at least in part, on the first virtual terrain, and
  - define a second virtual location of the first user in the virtual world based, at least in part, on the first virtual location and the second quantity or real-world activity performed by the first user, the second virtual location having a second virtual terrain, the second virtual terrain more difficult than the first virtual terrain.

19. The apparatus of claim 14, the network module further configured to receive, from at least one of a healthcare provider or a health insurance provider, a signal associated with the fitness of the first user and a fitness of the second user, the first scaling factor based, at least in part, on the fitness of the first user, the second scaling factor based, at least in part, on the fitness of the second user.

20. The apparatus of claim 14, further comprising:
- a virtual world module operatively coupled to the scaling module, the virtual world module configured to define a virtual world having a virtual terrain and a virtual path, the first user having a position on the virtual path, the first scaling factor based, at least in part, on the virtual terrain at the position of the first user.

\* \* \* \* \*